United States Patent
Ward

(10) Patent No.: US 12,150,890 B1
(45) Date of Patent: Nov. 26, 2024

(54) COOLING PACK FOR HEMORRHOIDS

(71) Applicant: Tonya Ward, Dorchester, MA (US)

(72) Inventor: Tonya Ward, Dorchester, MA (US)

( * ) Notice: Subject to any disclaimer, the term of this patent is extended or adjusted under 35 U.S.C. 154(b) by 622 days.

(21) Appl. No.: 17/494,043

(22) Filed: Oct. 5, 2021

(51) Int. Cl.
*A61F 7/10* (2006.01)
*A61F 7/00* (2006.01)
*A61F 7/02* (2006.01)
*A61F 7/12* (2006.01)

(52) U.S. Cl.
CPC .............. *A61F 7/10* (2013.01); *A61F 7/12* (2013.01); *A61F 2007/0028* (2013.01); *A61F 2007/0219* (2013.01); *A61F 2007/0222* (2013.01); *A61F 2007/108* (2013.01)

(58) Field of Classification Search
CPC .............. A61F 7/10; A61F 2007/0028; A61F 2007/0126
See application file for complete search history.

(56) References Cited

U.S. PATENT DOCUMENTS

| 4,240,436 | A | * | 12/1980 | Singleton | A61F 7/10 607/108 |
| 5,707,645 | A | * | 1/1998 | Wierson | A61F 7/10 604/113 |
| 5,935,595 | A | * | 8/1999 | Steen | A61F 7/10 602/41 |
| D667,115 | S | | 9/2012 | Caballero | |
| 9,545,391 | B2 | | 1/2017 | Rosenblum | |
| 9,592,150 | B2 | | 3/2017 | McNulty, Jr. | |
| 2002/0147482 | A1 | * | 10/2002 | Carter | A61F 7/02 607/108 |
| 2004/0126412 | A1 | | 7/2004 | Halloran | |
| 2011/0300124 | A1 | | 12/2011 | Thornton | |
| 2013/0046328 | A1 | | 2/2013 | Bourque | |
| 2014/0371829 | A1 | | 12/2014 | Stine | |
| 2015/0018763 | A1 | | 1/2015 | Lee | |
| 2017/0056332 | A1 | | 3/2017 | Ayala | |
| 2020/0000631 | A1 | * | 1/2020 | Herzka | A61F 7/02 |

FOREIGN PATENT DOCUMENTS

WO     2017040420     3/2017

\* cited by examiner

*Primary Examiner* — Kaitlyn E Smith
(74) *Attorney, Agent, or Firm* — Kyle A. Fletcher, Esq.

(57) ABSTRACT

The cooling pack for hemorrhoids is a medical device. The cooling pack for hemorrhoids is a therapeutic device. The cooling pack for hemorrhoids is adapted for use in the treatment of a hemorrhoid. The cooling pack for hemorrhoids is a thermal pack. The cooling pack for hemorrhoids is cooled below −15 degrees C. The cooling pack for hemorrhoids forms a therapeutic structure that is placed against the hemorrhoid while cold. The cooling pack for hemorrhoids comprises a shell and a thermal gel. The shell forms a containment structure that encloses the thermal gel. The thermal gel is a chemical with a high thermal capacity. The thermal gel provides a heat exchange medium that rapidly cools the hemorrhoid when placed against the hemorrhoid.

13 Claims, 5 Drawing Sheets

COOLING PACK FOR HEMORRHOIDS

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical devices including devices for heating and cooling the body, more specifically, a device for cooling internal body cavities. (A61F7/12)

SUMMARY OF INVENTION

The cooling pack for hemorrhoids is a medical device. The cooling pack for hemorrhoids is a therapeutic device. The cooling pack for hemorrhoids is adapted for use in the treatment of a hemorrhoid. The cooling pack for hemorrhoids is a thermal pack. The cooling pack for hemorrhoids is cooled below −15 degrees C. The cooling pack for hemorrhoids forms a therapeutic structure that is placed against the hemorrhoid while cold. The cooling pack for hemorrhoids comprises a shell and a thermal gel. The shell forms a containment structure that encloses the thermal gel. The thermal gel is a chemical with a high thermal capacity. The thermal gel provides a heat exchange medium that rapidly cools the hemorrhoid when placed against the hemorrhoid.

These together with additional objects, features and advantages of the cooling pack for hemorrhoids will be readily apparent to those of ordinary skill in the art upon reading the following detailed description of the presently preferred, but nonetheless illustrative, embodiments when taken in conjunction with the accompanying drawings.

In this respect, before explaining the current embodiments of the cooling pack for hemorrhoids in detail, it is to be understood that the cooling pack for hemorrhoids is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the cooling pack for hemorrhoids.

It is therefore important that the claims be regarded as including such equivalent construction insofar as they do not depart from the spirit and scope of the cooling pack for hemorrhoids. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
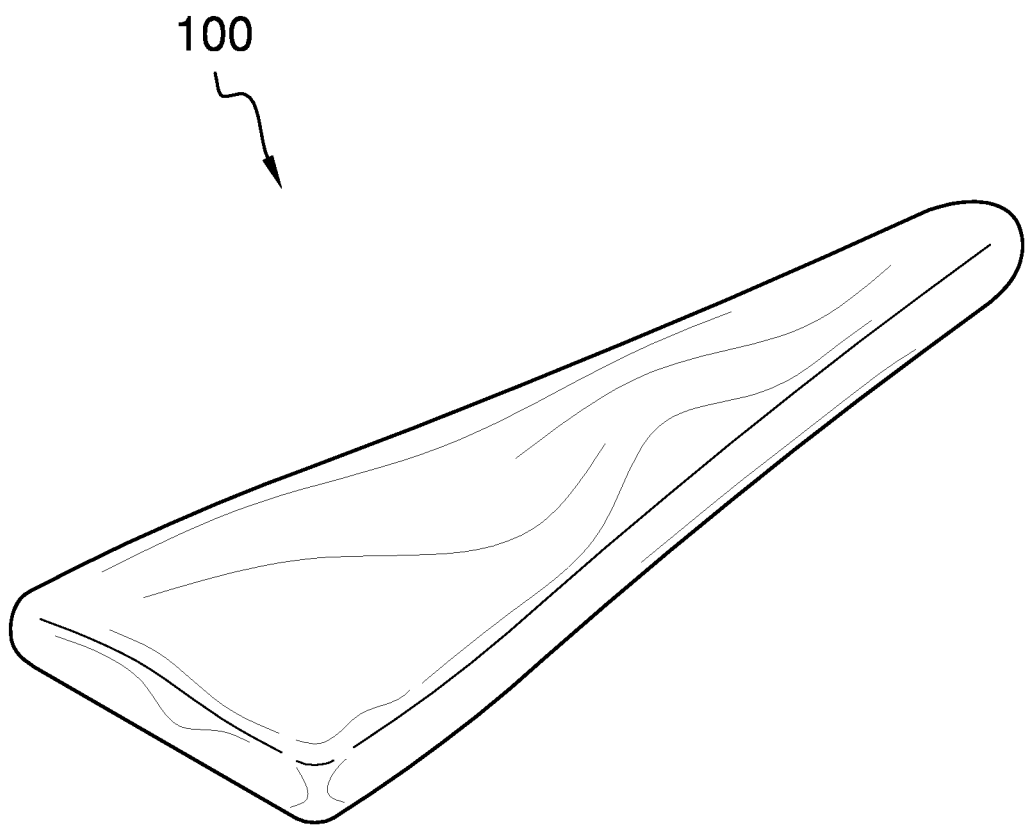
FIG. 1 is a perspective view of an embodiment of the disclosure.
Figure 2:
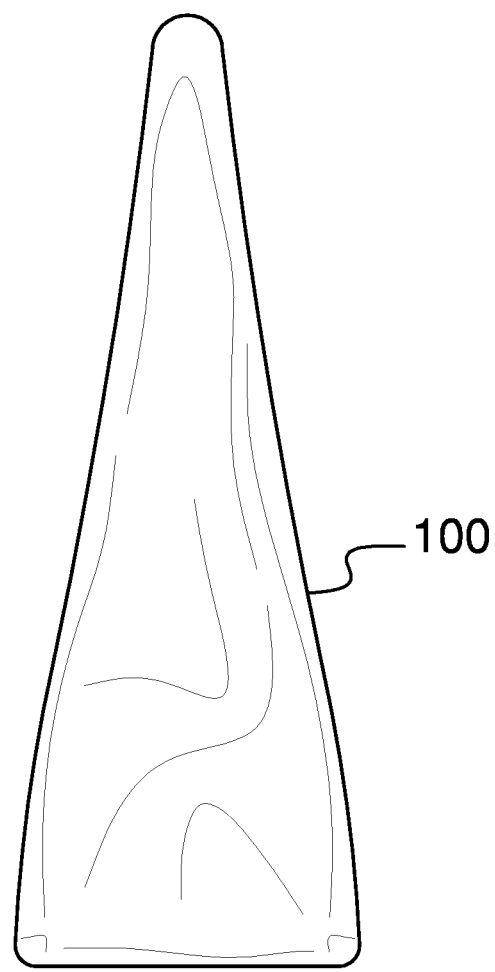
FIG. 2 is a front view of an embodiment of the disclosure.
Figure 3:
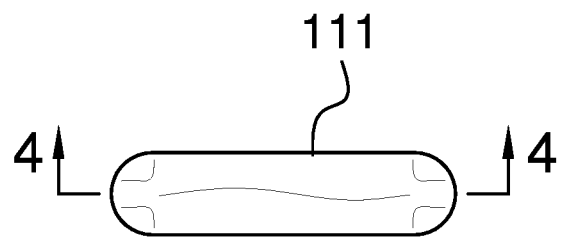
FIG. 3 is a side view of an embodiment of the disclosure.
Figure 4:
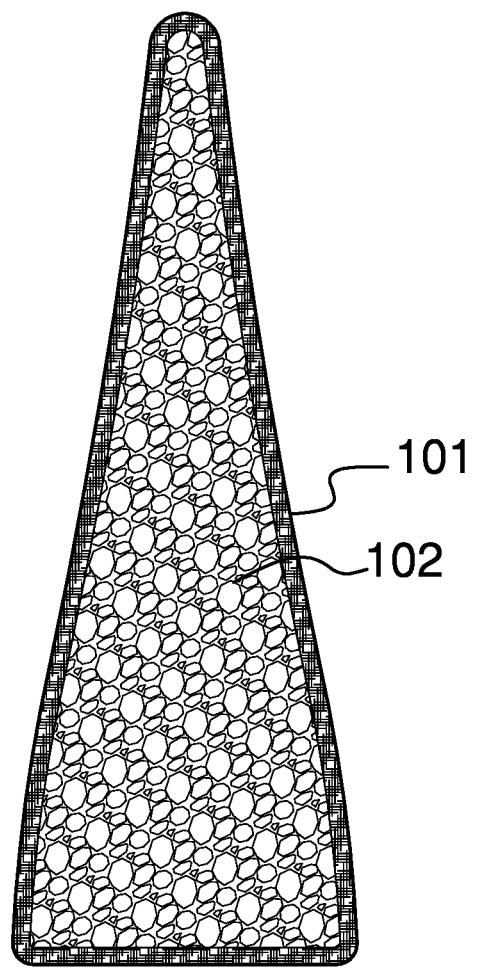
FIG. 4 is a cross-sectional view of an embodiment of the disclosure across 4-4 as shown in FIG. 3.
Figure 5:
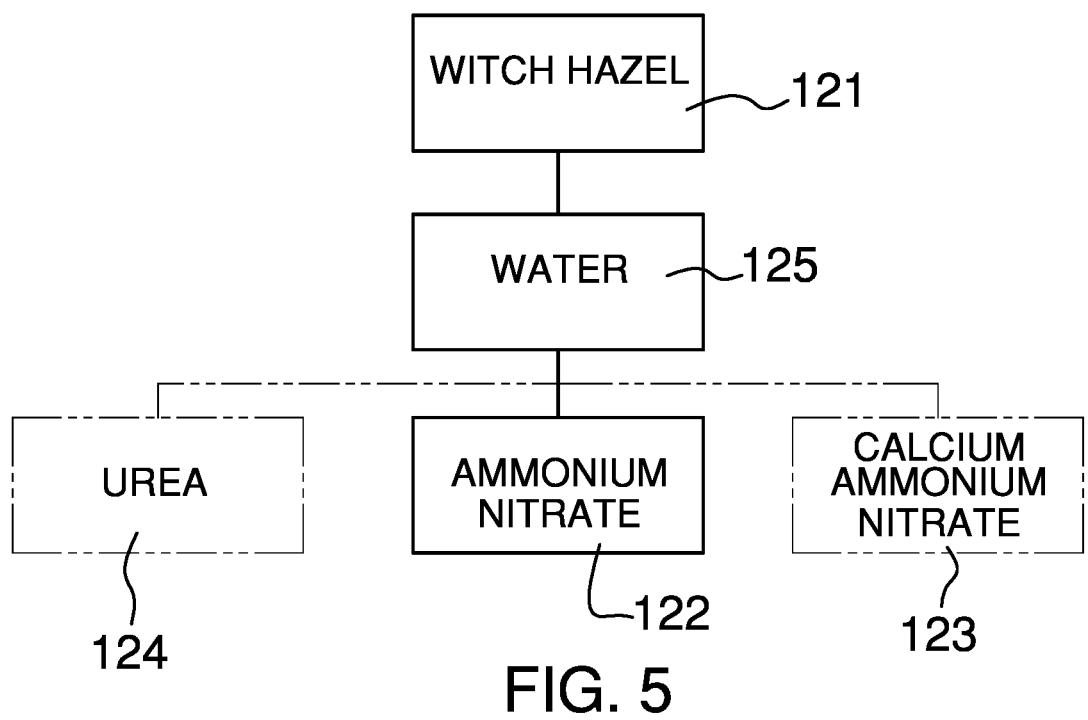
FIG. 5 is a schematic view of an embodiment of the disclosure.
Figure 6:
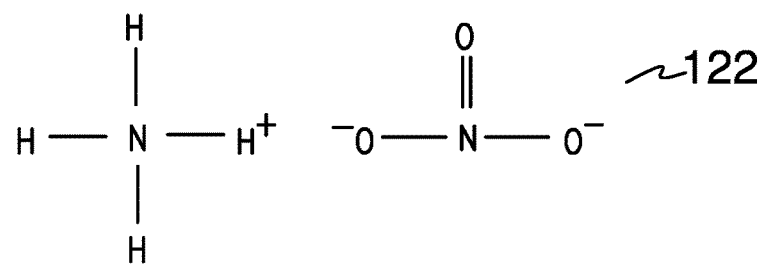
FIG. 6 is a chemical diagram of an embodiment of the disclosure.
Figure 6:
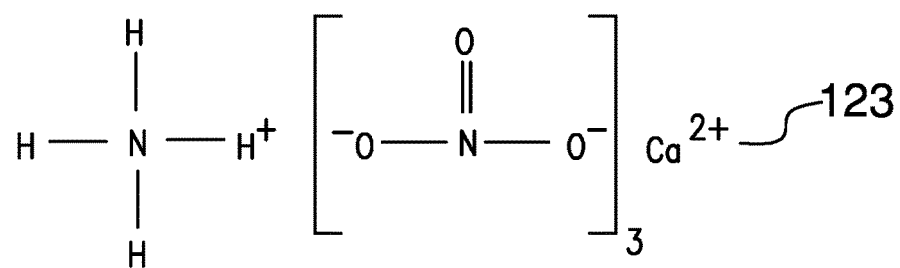
Figure 6:
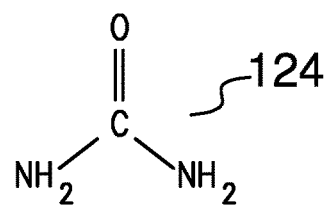
Figure 6:
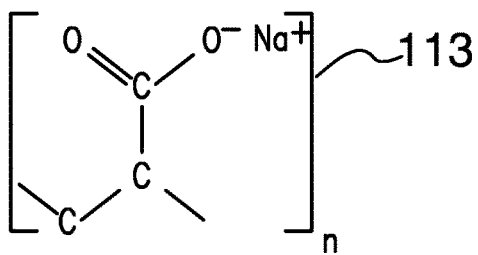
Figure 6:
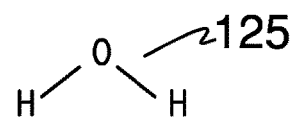
Figure 6:
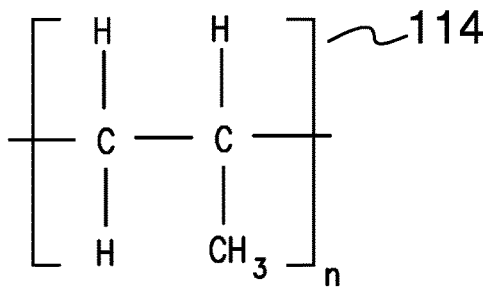
Figure 6:
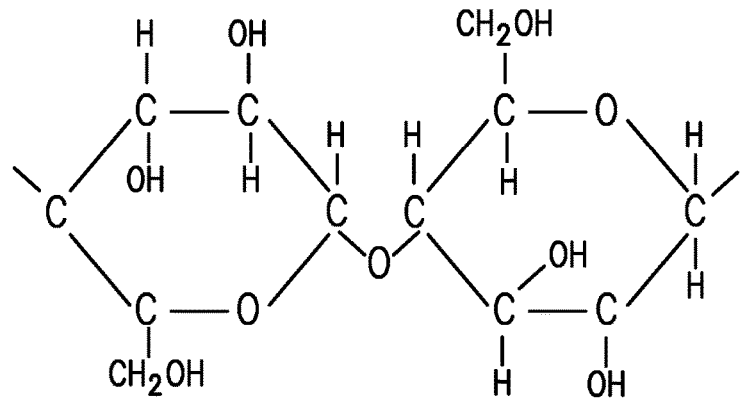

Detailed reference will now be made to one or more potential embodiments of the disclosure, which are illustrated in FIGS. 1 through 6.

The cooling pack for hemorrhoids 100 (hereinafter invention) is a medical device. The invention 100 is a therapeutic device. The invention 100 is adapted for use in the treatment of a hemorrhoid. The invention 100 is a thermal pack. The invention 100 is cooled below −15 degrees C. The invention 100 forms a therapeutic structure that is placed against the hemorrhoid while cold. The invention 100 comprises a shell 101 and a thermal gel 102. The shell 101 forms a containment structure that encloses the thermal gel 102. The thermal gel 102 is a chemical with a high thermal capacity. The thermal gel provides a heat exchange medium that rapidly cools the hemorrhoid when placed against the hemorrhoid.

The shell 101 is a containment structure. The shell 101 forms a membrane structure that encloses the thermal gel 102. The membrane formed by the shell 101 is a flexible structure. The shell 101 is an absorbent structure such that the shell 101 will absorb water 125 away from the hemorrhoid during the therapeutic session. The shell 101 comprises a disk structure 111.

The disk structure 111 is a triangular disk shaped structure. The disk structure 111 forms the containment structure of the shell 101 that stores the thermal gel 102. The disk structure 111 provides a large surface area relative to the volume of thermal gel 102 such that the heat transfer between the hemorrhoid and the thermal gel 102 is maximized.

The shell 101 further comprises a cellulose (CAS: 9004-34-6) 112, a sodium polyacrylate (CAS: 9003 April 7) 113, a polypropylene (CAS: 9003 April 7) 114, and a water 125. The cellulose (CAS: 9004-23 34-6) 112, the sodium polyacrylate (CAS: 9003 April 7) 113, and the polypropylene (CAS: 9003 April 7) 114 are each a polymer structure that forms a cross-linked mesh structure. The mesh structure formed by the cellulose (CAS: 9004-34-6) 112, the sodium polyacrylate (CAS: 9003 April 7) 113, and the polypropylene (CAS: 9003 April 7) 114 forms a flexible gel structure. The flexible gel structure formed by the cellulose (CAS: 9004-34-6) 112, the sodium polyacrylate (CAS: 9003 April 7) 113, and the polypropylene (CAS: 9003 April 7) 114 forms the exterior surfaces of the shell 101.

The cellulose (CAS: 9004-34-6) 112 is a phytochemical. The cellulose (CAS: 9004-34-6) 112 is a starch based polymer. The cellulose (CAS: 9004-34-6) 112 is defined elsewhere in this disclosure.

The sodium polyacrylate (CAS: 9003 April 7) 113 is a super absorbent polymer. The super absorbent polymer is defined elsewhere in this disclosure. The sodium polyacrylate (CAS: 9003 April 7) 113 provides the disk structure 111 with the capacity to wick water 125 away from the hemorrhoid. The sodium polyacrylate (CAS: 9003 April 7) 113 is formed from an acrylate polymer base structure. The acrylate polymer structure is modified with sodium to form a water 125 absorbing salt. The sodium polyacrylate (CAS: 9003 April 7) 113 is defined elsewhere in this disclosure.

The polypropylene (CAS: 9003 April 7) 114 is a synthetic structure. The polypropylene (CAS: 9003 April 7) 114 is a polymer based structure. The polypropylene (CAS: 9003 April 7) 114 is defined elsewhere in this disclosure.

The thermal gel 102 is a chemical structure. The thermal gel 102 is a solution with a high thermal capacity. The thermal gel 102 forms the thermal structure that cools the hemorrhoid during the therapeutic process. The thermal gel 102 is cooled to −15 degrees C. during the cooling of the invention 100. The thermal gel 102 draws heat away from the hemorrhoid when the surface of the shell 101 is placed against the hemorrhoid. The thermal gel 102 comprises a witch hazel 121, an ammonium nitrate (CAS: 6484-52-2) 122, a calcium ammonium nitrate (CAS: 15245 December 2) 123, a urea (CAS: 57-13-6) 124, and water 125.

The witch hazel 121 is a phytochemical substance derived from plants in the witch hazel 121 family. The witch hazel 121 is known as a pharmacologically active media that includes tannic acid. The witch hazel 121 is mixed with the water 125 to form a solvent that dissolves and coagulates the ammonium nitrate (CAS: 6484-52-2) 122, the calcium ammonium nitrate (CAS: 15245 December 2) 123, and the urea (CAS: 57-13-6) 124. The role of the witch hazel 121 in the thermal gel 102 is to control the coagulation of the ammonium nitrate (CAS: 6484-52-2) 122, the calcium ammonium nitrate (CAS: 15245 December 2) 123, and the urea (CAS: 57-13-6) 124 into beads within the witch hazel 121 and water 125 solution. By controlling the coagulation levels, and the resulting bead sizes, of the ammonium nitrate (CAS: 6484-52-2) 122, the calcium ammonium nitrate (CAS: 15245 December 2) 123, and the urea (CAS: 57-13-6) 124, the witch hazel 121 ensures that the thermal gel 102 chills evenly through the invention 100.

The ammonium nitrate (CAS: 6484-52-2) 122 is a chemical structure that is suspended within the witch hazel 121 and the water 125 solution. The calcium ammonium nitrate (CAS: 15245 December 2) 123 is a chemical structure that is suspended within the witch hazel 121 and the water 125 solution. The ammonium nitrate (CAS: 6484-52-2) 122 and the calcium ammonium nitrate (CAS: 15245 December 2) 123 are defined elsewhere in this disclosure. The urea (CAS: 57-13-6) 124 is a chemical structure that is suspended within the witch hazel 121 and the water 125 solution.

The following definitions were used in this disclosure:

Alkaloid: As used in this disclosure, an alkaloid refers to a chemical with a molecular structure that contains one or more heterocyclic rings. The alkaloid generally has a high pH (i.e. is a basic substance). An alkaloid is typically soluble in water with a low (acidic) pH and soluble in lipids with a neutral or high (basic) pH.

Ammonium Nitrate: As used in this disclosure, ammonium nitrate (CAS 6484-52-2) refers to a chemical compound with the formula NH3HNO3. Ammonium nitrate is a common name for nitric acid ammonium salt. Ammonium nitrate is commonly used for fertilizer and as an oxidizing agent in explosives. Dissolving ammonium nitrate in water results in a rapid endothermic reaction. This reaction is used in the creation of commercially available "instantly" available cold packs. Ammonium nitrate is commonly marketed as a mixture of ammonium nitrate and calcium nitrate (CAS 10124-37-5). The calcium nitrate reduces the oxidizing potential of the ammonium nitrate such that the ammonium nitrate is not considered an oxidizing agent under United States Department of Transportation regulations. The introduction of calcium nitrate into the ammonium nitrate does not reduce the effectiveness of the ammonium nitrate as a fertilizer or the use of ammonium nitrate in endothermic reactions.

Biological Alkaloid: As used in this disclosure, a biological alkaloid is a class of phytochemical. The biological alkaloid is identified as phytochemical that contains one or more alkaloid structures. The biological alkaloid are believed to provide benefits. Most biological alkaloids act as either a depressant (for example morphine (CAS 57-27-2)) or stimulant (for example caffeine (CAS 58-08-2)) to the nervous system. Biological alkaloids are also effective in disrupting the cellular membranes of microorganisms including evolved viruses.

Biological Thiol: As used in this disclosure, a biological thiol is a class of phytochemical. The biological thiol is identified as a thiol functional group that is attached to a phytochemical. In general, all biological thiols act as an antioxidant. The biological thiols include, but are not limited to, glutathione (CAS 70-18-8), N-Acetylcysteine (CAS 619-91-1; Abbreviated NAC), and captopril (CAS 62571-82-2). Glutathione (CAS 70-18-8) is a pharmacologically active media that believed to provide benefits: a) in metabolic regulation; and, b) as a chemical modulator in the neurotransmission process. N-Acetylcysteine (CAS 619-91-1) is a pharmacologically active media that believed to provide therapeutic benefits by breaking up accumulations of mucus in the lungs. There are preliminary findings that N-Acetylcysteine (CAS 619-91-1) may be an effective treatment for mild psychiatric disorders. Captopril (CAS 62571-82-2) is a pharmacologically active media that believed to provide benefits in the treatment of hypertension.

Cellulose: As used in this disclosure, a cellulose (CAS: 9004-34-6) is a carbohydrate formed from monomers of beta-D-glucose (CAS 492-61-5) molecules. Cellulose is an insoluble substance that is the main constituent of plant cell walls and vegetable fibers such as cotton.

Chemical: As used in this disclosure, a chemical refers to a substance of a known or fixed composition. The term chemical is used to describe the substance when the details of the composition of the substance or properties of the substance are considered relevant to the disclosure at bar.

The term properties is taken to mean both the measurable properties of the substance and the interactions of a first chemical with a second chemical. The term compound refers to: a) a chemical structure that comprises a one or more chemical bonds; or, b) a unified chemical structure formed from mixture of chemicals. The term compound is informally considered a synonym for the term chemical. The term chemistry refers to the study and the use of the knowledge of the composition and properties of chemicals. The term chemical reaction refers to the interactions between two or more chemical structures.

Chemical Bond: As used in this disclosure, a chemical bond refers to an attractive force between a first molecule or atom and a second molecule or atom. The primary bonds include, but are not limited to, covalent bonds, ionic bonds, and hydrogen bonds.

Combustion: As used in this disclosure, combustion refers to a reduction-oxidation reaction wherein oxygen and a hydrocarbon are combined to release energy, carbon dioxide, and water. In general usage, the meaning of combustion is often extended to describe a reaction between oxygen and a fuel source, such as a hydrocarbon modified by functional groups, which releases energy.

Cosmetic Media: As used in this disclosure, a cosmetic media refers to a chemical substance that is topically applied to a biological organism. The purposes for a cosmetic media include, but are not limited to: a) cleaning the skin and the hair of the biological organism; b) changing the visual, olfactory, and tactile stimuli presented by the biological organism to other nearby biological organisms; and, c) the topical application of a pharmacologically active media.

Covalent Bond: As used in this disclosure, a covalent bond refers to a chemical bond between a first atom and a second atom wherein the first atom and the second atom share each share one or more electrons with each other. This is in contrast to an ionic bond.

Dimer: As used in this disclosure, a dimer refers to the bonding of two or more identical molecules to each other.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk. In this disclosure, the congruent ends of the prism-shaped structure that forms the disk are referred to as the faces of the disk.

Elastic: As used in this disclosure, an elastic is a material or object that deforms when a force is applied to it and that is able to return to its relaxed shape after the force is removed. A material that exhibits these qualities is also referred to as an elastomeric material. A material that does not exhibit these qualities is referred to as inelastic or an inelastic material.

Flavonoid: As used in this disclosure, a flavonoid is a phytochemical. The flavonoid comprises a collection of functional groups attached to a chemical backbone selected from the group consisting of: a) the flavone (CAS 525-82-6) chemical group; b) the isoflavone chemical group (CAS 446-72-0); and, c) the neoflavonoid (CAS 51870-64-5) chemical group. Anthocyanins are a common subclass of flavonoid based on the flavone chemical group.

Flexible: As used in this disclosure, flexible refers to an object or material that will deform when a force is applied to it but that will not necessarily return to its original shape when the deforming force is removed.

Gel: As used in this disclosure, a gel is a substance comprising mostly of liquid (by mass) that is trapped in a cross-linked network structure that exhibits the properties of both a solid and a liquid.

Heat: As used in this disclosure, heat refers to a transfer of energy between a first object and a second object such that the temperatures of the first object and the second object of one or both of the objects changes. In common usage, heat is said to flow from the warmer object to the cooler object. In systems where the combined energies of the first object and the second object remain constant, the equilibrium temperatures of the first object and the second object will be equal.

Hydrocarbon: As used in this disclosure, a hydrocarbon is a molecule comprising hydrogen and oxygen. Alkanes, alkenes, and alkynes are examples of hydrocarbons.

Hydrogen Bond: As used in this disclosure, a hydrogen bond refers to an electrostatic attraction between: 1) a cation and an anion; 2) a cation and a negative dipole; or, 3) an anion and a positive dipole. The exchange of electrons (as would occur in an ionic bond or covalent bond) does not occur in a hydrogen bond. As a rule, the energy to break an ionic bond is less that the energy required to break a covalent bond or an ionic bond.

Ionic Bond: As used within this disclosure, an ionic bond refers to a chemical bond between a first atom and a second atom wherein the first atom takes an electron from the second atom. This is in contrast to a covalent bond.

Lipid: As used in this disclosure, a lipid is an organic molecule that is soluble in nonpolar solvents.

Non-Polar Molecule: As used in this disclosure, a non-polar molecule refers to a molecular structure that: a) is electrically neutral; and, b) has a uniform spatial distribution of the electrons within the molecule.

Organic: As used in this disclosure, organic refers to a carbon-based chemical structure. A limited number of carbon-based salts are traditionally considered inorganic chemical structures and are excluded from the study of organic chemistry.

Pharmacologically Active Media: As used in this disclosure, a pharmacologically active media refers to a chemical substance that has a biochemical or physiological effect on a biological organism.

Phytochemical: As used in this disclosure, a phytochemical is a pharmacologically active media that is produced in and harvested from a plant. Within this disclosure, a phytochemical comprises a pharmacologically active media containing one or more chemical groups selected from the group consisting of: a) the flavonoid chemical group; b) the terpenoid chemical group (including the carotenoid chemical subgroup of the terpenoid chemical group); c) polyphenol chemical group; d) the polyacetylene chemical group; e) the biological thiol chemical group; and, f) the biological alkaloid chemical group.

Polar Molecule: As used in this disclosure, a polar molecule refers to a molecular structure that: a) is electrically neutral; but, b) does not have a uniform spatial distribution of the electrons within the molecule. A polar molecule will present one or more electrically positive poles and the same number of electrically negative poles within the molecular structure.

Polarity: As used in this disclosure, the term polarity is used to describe a physical property or physical characteristic wherein: 1) the physical property or physical characteristic manifests two opposing attributes, tendencies, characteristics, or principals; and, 2) the two opposing attributes, tendencies, characteristics, or principals have an intrinsic separation, alignment, or orientation.

Polyacetylene: As used in this disclosure, a polyacetylene is a phytochemical. The polyacetylene comprises a collection of functional groups attached to a chemical backbone that is formed from, or contains, one or more chains built from the (C2H2) n polymer where n>=2.

Polyphenol: As used in this disclosure, a polyphenol is a phytochemical. The polyphenol comprises a collection of functional groups attached to a chemical backbone formed from two or more phenol (CAS 108-95-2) molecules. A lignan refers to a dimer containing two or more identical molecules that contain a phenol.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Relaxed Shape: As used in this disclosure, a structure is considered to be in its relaxed state when no shear, strain, or torsional forces are being applied to the structure.

Salt: As used in this disclosure, a salt means an ionic compound that further comprises at least one atom of a metallic element or compound and one atom of a non-metallic element or compound. When dissolved in water, the ionic compound releases the metallic element and the non-metallic element into the water as ions. In this disclosure, a metallic element is assumed to include the alkali metals and the alkali earth metals. Alternatively, and equivalently, a metallic element may be assumed to be any element on the periodic table that is to the left of the metalloids.

Solution: As used in this disclosure, a solution is a uniform mixture of two or more compounds in a liquid phase. The major component selected from the two or more compounds that forms the solution is called the solvent. The components remaining in the two or more compounds are called the solute. A polar solvent is a solvent formed from polar molecules. A non-polar solvent is a solvent formed from non-polar molecules. The rule of thumb that "like dissolves like" states that: a) solutes formed from polar molecules will dissolve in polar solvents but will not dissolve in non-polar solvents; and, b) solutes formed from non-polar molecules will dissolve in non-polar solvents but will not dissolve in polar solvents.

Super Absorbent Polymer: As used in this disclosure, a super absorbent polymer is a polymer that is used as a dehydrating chemical that absorbs/captures water. This disclosure assumes that a superabsorbent polymer captures over at least 50 times its mass in water and over 30 times its volume in water. The capture of water by a super absorbent polymer usually forms a hydrogel. A commonly used super absorbent polymer is sodium polyacrylate (CAS 9003 April 7).

Tannic Acid: As used in this disclosure, tannic acid refers to a naturally occurring chemical substance based on tannins. The primary co-polymer molecule that forms tannic acid is 1,2,3,4,6-penta-O-(3,4-dihydroxy-5-[(3,4,5-trihydroxybenzoyl)oxy]benzoyl)-D-glucopyranose (CAS 1401-55-04). Tannic acid is also an informal name for 1,2,3,4,6-penta-O-(3,4-dihydroxy-5-[(3,4,5-trihydroxybenzoyl)oxy] benzoyl)-D-glucopyranose. Tannic acid is one of the naturally occurring ingredients in Witch Hazel. Tannic acid is believed to have anti-coagulant properties.

Terpenoid: As used in this disclosure, a terpenoid is a phytochemical. The terpenoid comprises a collection of functional groups attached to a chemical backbone of a terpene. The terpene is a chemical structure formed from an integer number of isoprene (CAS 78-79-5) molecules. The functional groups attached to the terpenoid will always include at least one hydroxyl (alcohol) group.

Therapeutic: As used in this disclosure, therapeutic is an adjective that refers to a medical, ameliorative, or hygienic substance, process, procedure, or device.

Thermal Pack: As used in this disclosure, a thermal pack is an enclosed bag that contains a mass of material that has a high thermal capacity. The thermal pack is commonly used to rapidly warm and cool objects. A thermal pack used strictly for cooling is referred to as an ice pack. A thermal pack used strictly for heating is a hot pack.

Thermal Capacity: As used in this disclosure, the thermal capacity of a material is a measure of the energy required to be added to the material to raise the temperature of the material by a previously specified amount. The heat capacity of a material, also known as the specific heat, refers to the thermal capacity after normalization for potential differences in mass.

Thiol: As used in this disclosure, a thiol is a functional group formed with hydrosulfide (also known as bisulfide). The ionic chemical formula HS(−). As a functional group, the thiol has the chemical formula of RSH.

Topical: As used in this disclosure, topical is an adjective that is associated with a media selected from the group consisting of a pharmacologically active media and a cosmetic media. Topical indicates that the pharmacologically active media is applied directly to the skin.

Water: As used in this disclosure, water (CAS 7732-18-5) is a molecule comprising two hydrogen atoms and one oxygen molecule. The phase of water at normal temperature and pressure is liquid. As used in this disclosure, the definition of water is expanded to include dilute water-based solutions of salts and ionic structures using water as the solvent. Water in a gas phase is often referred to as steam. Water in a solid phase is often referred to as ice. Snow refers to a bulk solid form of ice.

With respect to the above description, it is to be realized that the optimum dimensional relationship for the various components of the invention described above and in FIGS. 1 through 6 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, The inventor claims:

1. A cooling pack for hemorrhoids comprising
   wherein the cooling pack for hemorrhoids comprises a shell and a thermal gel;
   wherein the shell forms a containment structure that encloses the thermal gel;
   wherein the shell further comprises a cellulose (CAS: 9004-34-6), a sodium polyacrylate (CAS: 9003 April 7), a polypropylene (CAS: 9003 April 7), and a water;
   wherein the cellulose (CAS: 9004-34-6), the sodium polyacrylate (CAS: 9003 April 7), and the polypropylene (CAS: 9003 April 7) are each a polymer structure that forms a cross-linked mesh structure;
   wherein the mesh structure formed by the cellulose (CAS: 9004-34-6), the sodium polyacrylate (CAS: 9003 April 7), and the polypropylene (CAS: 9003 April 7) Forms a flexible gel structure;
   wherein the flexible gel structure formed by the cellulose (CAS: 9004-34-6), the sodium polyacrylate (CAS: 9003 April 7), and the polypropylene (CAS: 9003 April 7) Forms the exterior surfaces of the shell.

2. The cooling pack for hemorrhoids according to claim 1
   wherein the cooling pack for hemorrhoids is a medical device;
   wherein the cooling pack for hemorrhoids is a therapeutic device;
   wherein the cooling pack for hemorrhoids is adapted for use in the treatment of a hemorrhoid;
   wherein the cooling pack for hemorrhoids is a thermal pack;
   wherein the cooling pack for hemorrhoids is cooled;
   wherein the cooling pack for hemorrhoids forms a therapeutic structure that is placed against the hemorrhoid while cold.

3. The cooling pack for hemorrhoids according to claim 2
   wherein the thermal gel is a chemical with a high thermal capacity;
   wherein the thermal gel provides a heat exchange medium that cools the hemorrhoid when placed against the hemorrhoid.

4. The cooling pack for hemorrhoids according to claim 3
   wherein the shell forms a membrane structure that encloses the thermal gel;
   wherein the membrane structure is flexible.

5. The cooling pack for hemorrhoids according to claim 4 wherein the shell is an absorbent structure such that the shell will absorb water away from the hemorrhoid during a therapeutic session.

6. The cooling pack for hemorrhoids according to claim 5
   wherein the shell comprises a disk structure;
   wherein the disk structure is a triangular disk shaped structure;
   wherein the disk structure forms the containment structure of the shell that stores the thermal gel.

7. The cooling pack for hemorrhoids according to claim 6
   wherein the thermal gel is a chemical structure;
   wherein the thermal gel is a solution with a high thermal capacity;
   wherein the thermal gel forms a thermal structure that cools the hemorrhoid during a therapeutic process;
   wherein the thermal gel draws heat away from the hemorrhoid when the surface of the shell is placed against the hemorrhoid.

8. The cooling pack for hemorrhoids according to claim 7
   wherein the thermal gel comprises a witch hazel, an ammonium nitrate (CAS: 6484-52-2), a calcium ammonium nitrate (CAS: 15245 December 2), a urea (CAS: 57-13-6), and water;
   wherein the witch hazel is mixed with the water to form a solvent that dissolves and coagulates the ammonium nitrate (CAS: 6484-52-2), the calcium ammonium nitrate (CAS: 15245 December 2), and the urea (CAS: 57-13-6).

9. The cooling pack for hemorrhoids according to claim 8
   wherein the witch hazel is a phytochemical substance derived from plants in the witch hazel family;
   wherein the witch hazel is known as a pharmacologically active media that includes tannic acid;
   wherein the witch hazel controls the coagulation of the ammonium nitrate (CAS: 6484-52-2), the calcium ammonium nitrate (CAS: 15245 December 2), and the urea (CAS: 57-13-6) into beads within the witch hazel and water solution.

10. The cooling pack for hemorrhoids according to claim 9
    wherein the ammonium nitrate (CAS: 6484-52-2) is a chemical structure that is suspended within the witch hazel and the water solution;
    wherein the calcium ammonium nitrate (CAS: 15245 December 2) is a chemical structure that is suspended within the witch hazel and the water solution;
    wherein the urea (CAS: 57-13-6) is a chemical structure that is suspended within the witch hazel and the water solution.

11. The cooling pack for hemorrhoids according to claim 10
    wherein the cellulose (CAS: 9004-34-6) is a phytochemical;
    wherein the cellulose (CAS: 9004-34-6) is a starch based polymer.

12. The cooling pack for hemorrhoids according to claim 11
    wherein the sodium polyacrylate (CAS: 9003 April 7) is a super absorbent polymer;
    wherein the sodium polyacrylate (CAS: 9003 April 7) provides the disk structure with the capacity to wick water away from the hemorrhoid;
    wherein the sodium polyacrylate (CAS: 9003 April 7) is formed from an acrylate polymer base structure;
    wherein the acrylate polymer structure is modified with sodium to form a water absorbing salt.

13. The cooling pack for hemorrhoids according to claim 12
    wherein the polypropylene (CAS: 9003 April 7) is a synthetic structure;
    wherein the polypropylene (CAS: 9003 April 7) is a polymer based structure.

* * * * *